(12) United States Patent
Lee et al.

(10) Patent No.: US 8,311,184 B2
(45) Date of Patent: Nov. 13, 2012

(54) FAN-SHAPED X-RAY BEAM IMAGING SYSTEMS EMPLOYING GRADED MULTILAYER OPTIC DEVICES

(75) Inventors: Susanne Madeline Lee, Cohoes, NY (US); Peter Michael Edic, Albany, NY (US); Forrest Frank Hopkins, Cohoes, NY (US)

(73) Assignee: General Electric Company, Niskayuna, NY (US)

( * ) Notice: Subject to any disclaimer, the term of this patent is extended or adjusted under 35 U.S.C. 154(b) by 256 days.

(21) Appl. No.: 12/871,484

(22) Filed: Aug. 30, 2010

(65) Prior Publication Data

US 2012/0051499 A1 Mar. 1, 2012

(51) Int. Cl.
*G21K 1/06* (2006.01)
(52) U.S. Cl. ............................... 378/84; 378/16
(58) Field of Classification Search .................. 378/16, 378/73, 82, 84, 85, 145, 156
See application file for complete search history.

(56) References Cited

U.S. PATENT DOCUMENTS

| | | | |
|---|---|---|---|
| 5,192,869 A | 3/1993 | Kumakhov | |
| 5,604,353 A | 2/1997 | Gibson et al. | |
| 6,934,359 B2 | 8/2005 | Chen et al. | |
| 6,935,778 B2 | 8/2005 | Bievenue et al. | |
| 7,366,374 B1 | 4/2008 | Lee et al. | |
| 7,412,131 B2 | 8/2008 | Lee et al. | |
| 7,508,911 B1 | 3/2009 | Lee et al. | |
| 2005/0094271 A1 | 5/2005 | Hoghoj | |
| 2005/0117239 A1 | 6/2005 | Hoghoj et al. | |
| 2006/0018429 A1 | 1/2006 | Hoghoj et al. | |
| 2006/0062351 A1 | 3/2006 | Yokhin et al. | |
| 2009/0041198 A1 | 2/2009 | Price et al. | |
| 2009/0074146 A1 | 3/2009 | Lee et al. | |
| 2009/0147922 A1 | 6/2009 | Hopkins et al. | |

FOREIGN PATENT DOCUMENTS

WO 2009076111 A1 6/2009

OTHER PUBLICATIONS

Tournear et al., "Gamma-Ray Channeling in Layered Structures", IEEE, pp. 4282-4285, 2004.
E.Difabrizio et al; "Shaping X-rays by diffractive coded nano-optics"; vol. 67-68, Issue 1 (Jun. 2003); ISSN:0167-9317; ISSN:0167-9317; 2Pages.
Enzo M. Di Fabrizio; Dan Cojoc; Stefano Cabrini; Burkhard Kaulich; Thomas Wilhein and Jean Susini; "Novel diffractive optics for x-ray beam shaping"; DOI: 10.1117/12.452287; Date: Nov. 21, 2002; 2Pages.

*Primary Examiner* — Jurie Yun
(74) *Attorney, Agent, or Firm* — Scott J. Asmus

(57) ABSTRACT

An X-ray imaging system that produces one or more fan-shaped beams is described. The system includes a target for emitting X rays that includes at least one target focal spot, and one or more graded multilayer optic devices in optical communication with the target. The optics transmits at least a portion of the source X rays to produce the one or more fan-shaped beams. The graded multilayer optic devices include at least a first graded multilayer section for redirecting and transmitting X rays through total internal reflection. The graded multilayer section includes a high-index layer of material having a first complex refractive index $n_1$, a low-index layer of material having a second complex refractive index $n_2$, and a grading zone disposed between the high-index and low-index layers of material. The grading zone includes a grading layer having a third complex refractive index $n_3$ such that $Re(n_1) > Re(n_2) > Re(n_3)$.

20 Claims, 13 Drawing Sheets

FAN-SHAPED X-RAY BEAM IMAGING SYSTEMS EMPLOYING GRADED MULTILAYER OPTIC DEVICES

BACKGROUND OF THE INVENTION

This invention relates to X-ray imaging systems, and, in particular, to X-ray imaging systems employing optic devices to produce collimated, fan-shaped beams having desired spectral shape.

Imaging applications, such as CT and X-ray diffraction, require ever-increasing levels of flux. Increasing X-ray flux may be accomplished, for example, by focusing X-ray radiation emitted by an X-ray source. X rays may be focused by reflecting an incident X-ray beam from an interface using total internal reflection. The interface can be formed between a first material medium having $n_f$ as a complex refractive index, and a second material medium having $n_s$ as a complex refractive index. Typically, the first material medium may be air, and the second material medium may be a solid. Total internal reflection can be realized if the real part of the complex refractive index $n_s$ of the second medium is smaller than the real part of the complex refractive index $n_f$ of the first medium, and if the angle of incidence of the X ray with the interface is smaller than a critical angle $\theta_{CR}$ specified for total internal reflection. However, the conventional method of selecting materials for the first material medium, and second material medium, solely on the basis of the material indices of refraction produces only modest gains in reflectivity.

In addition to increasing flux levels, spectral shaping an X-ray spectrum is another requirement for optimizing the X-ray spectrum for particular applications. One common artifact in radiographic and tomographic imaging arises from the fact that the lower energy X rays in a typical Bremsstrahlung (polychromatic) spectrum are attenuated preferentially as the beam penetrates material. This effect, which leads to an increase in the mean energy of the beam as it penetrates the sample, introduces a non-linearity in the relationship between the strength of the transmitted beam and the amount of material penetrated. This non-linearity manifests as artifacts in images reconstructed from the attenuation data, such as those attributed to beam hardening in computed tomography. Utilizing an X-ray beam that has a reduced spread of energies can mitigate some of these artifacts. Particularly where beam intensity, with respect to the intensity in that same range of the original spectrum, has been held constant or augmented by the use of the optic, the use of a limited range of energies can provide a desired degree of attenuation for a particular application and can produce an optimum image in terms of spatial resolution and contrast sensitivity. The shaping of a spectrum from a polychromatic energy distribution to a more monochromatic distribution enables such improvements in X-ray image sets. In some cases, change in the spectral shape, for example, reducing either the relative proportion of low-energy or high-energy X rays, may provide for optimum imaging of a sample.

However, multi-energy X-ray imaging, sometimes referred to as dual-energy imaging or energy discrimination imaging, has its own benefits. For example, multi-energy X-ray imaging has been shown to furnish information on specific material compositions in scanned objects for security, industrial, and medical applications. Such energy discrimination imaging can be achieved in several ways, including the use of two or more different X-ray spectra, which is often the most feasible approach. A challenge lies in the sequential nature of such an examination, where image data are generated, for example, first with one spectrum and then with another spectrum. In one technique, an object of interest is scanned twice. A first complete projection data set is produced in the first scan for one energy and then a second complete projection data set is produced in the second scan for the second energy. For many applications where high throughput is critical, sample composition is dynamic, and/or sample positioning may preclude repetitive scanning, the logistics of physically scanning an object twice may be unacceptable.

Conventional multi-energy X-ray imaging applications have used source filtration and/or high voltage modulation for rapidly altering the spectral characteristics on a time scale comparable to the view-by-view sampling time in a typical imaging scan. Such filtration consists of rapidly and sequentially inserting filters of appropriate composition to preferentially attenuate relatively low X-ray energies. Such methodologies are limited in the degree to which attenuation can produce cleanly separated energy intervals, severely restricting the sensitivity of this approach for analyzing different materials. High voltage modulation to produce different spectral characteristics also has been implemented in some cases with limited success. There is a challenge in both approaches to mitigate registration differences in the projections that result from sample movement between data sets acquired at different energies, as well as a slight misalignment of the X-ray paths that traverse the object, as is incurred with modulating the X-ray beam on a sub-view basis.

Typically, fan-shaped beams are used in a wide variety of polychromatic X-ray imaging situations to furnish information on specific material composition in scanned objects for security, industrial, and medical applications. For example, fan-shaped X-ray beams are used in X-ray imaging, such as for mammographic and general radiographic imaging in the medical field; computed tomography imaging; tomosynthesis imaging; and X-ray diffraction imaging.

Most conventional X-ray sources have a single X-ray generation spot whose effective size and location are determined and/or limited by the anode thermal loading and relative angle of emission. The X-ray spot is typically collimated using tungsten or lead in the transaxial (fan angle) and axial (cone angle) imaging directions. To use 2D reconstruction algorithms for CT (i.e., filtered back-projection), the X-ray spot is collimated such that only thin, pseudo-planar, fan-shaped sheets of X rays illuminate the imaged object. As a result, only a small percentage of the available X-ray photons from the spot are used for imaging as most X rays strike the collimator plate and are absorbed. To utilize a higher percentage of the available X rays, the cone angle of the X-ray beam can be broadened; however, more complicated cone-beam reconstruction algorithms are needed to achieve acceptable image quality for targeted applications. Hence, there is a tradeoff of X-ray flux utilization versus reconstruction complexity that exists in any CT imaging systems.

It would thus be desirable to have a reflective multilayer configuration that can provide fan-shaped X-ray beams having a desired spectral shape of the X-ray beam for X-ray imaging applications.

BRIEF DESCRIPTION OF THE INVENTION

In one embodiment, an X-ray imaging system that produces one or more fan-shaped beams is provided. The X-ray system includes a target for emitting X rays upon being struck by electrons from an electron source. The target includes at least one target focal spot, and one or more graded multilayer optic devices in communication with the target to transmit at least a portion of the X rays through total internal reflection to produce the one or more fan-shaped beams. The graded multilayer optic devices include a first graded multilayer section for redirecting and transmitting X rays through total internal reflection. The first graded multilayer section includes a high-index layer of material comprising a first complex refractive index $n_1$ having a real part Re $(n_1)$ and an imaginary part $\beta_1$, a low-index layer of material having a second complex refractive index $n_2$ having a real part Re $(n_2)$ and an imaginary part $\beta_2$, and a grading zone disposed between said high-index layer of material and said low-index layer of material, the grading zone having a grading layer having a third complex real refractive index $n_3$ having a real part Re $(n_2)$ and an imaginary part $\beta_3$ such that $Re(n_1)>Re(n_3)>Re(n_2)$.

In another embodiment, a multi-energy X-ray imaging system that produces one or more fan-shaped beams is provided. The system includes an electron source, a target for forming X rays upon being struck by electrons from the electron source, a vacuum chamber housing the target, a window through which the X rays may exit the vacuum chamber, and at least one graded multilayer optic device configured to transmit a desired range of X-ray energies to produce the one or more fan-shaped beams. The graded multilayer optic device includes a first optic portion for redirecting first optic X rays through total internal reflection, and a second optic portion for redirecting second optic X rays, the second optic X rays being at a different energy level than the first optic X rays.

In yet another embodiment, a method for imaging an object is provided. The method includes emitting electron beams from at least one electron beam emitter towards a target having at least one target focal spot, and producing X rays from the target in response to being struck by the electron beam. Further, the method includes forming the X rays into one or more fan-shaped beams, wherein the fan-shaped beams are produced via total internal reflection of the X rays through one or more graded multilayer optic devices positioned such that at least one of the one or more graded multilayer optic devices is in communication with the at least one target focal spot. Furthermore, the method includes generating an image of the object by using the emitted X rays transmitted via the one or more graded multilayer optics.

DETAILED DESCRIPTION

Figure 1A:
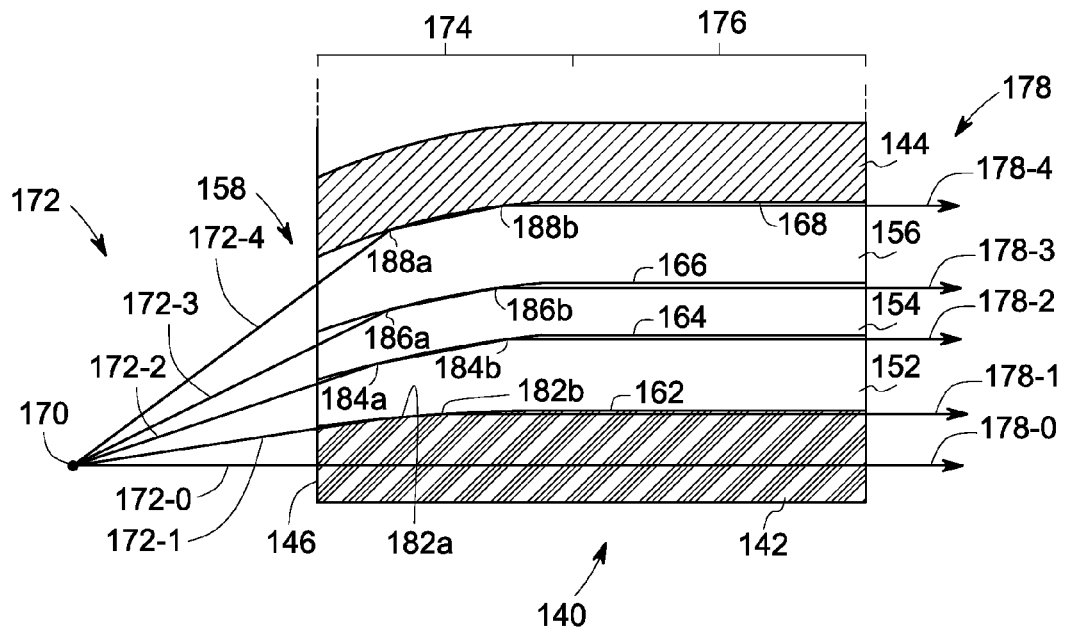
FIG. 1A is a detailed cross-sectional view of an exemplary embodiment of a single graded multilayer section comprising a high-index material layer, a grading zone on the high-index material layer, and a low-index layer on the grading zone, the graded multilayer section configured to include a redirection section and a collimation section.

This invention describes the use of one or more graded multilayer optic devices for redirecting at least some of the X rays from the X-ray source to produce a collimated, fan-shaped beam having a specified spectral shape. As used herein, the term "collimate" refers to the creation of quasi-parallel beams of X-ray radiation from divergent X-ray beams. In one example, the beam may be a fan-shaped beam for application (medical, industrial and/or security) in one or more of computed tomography (CT) imaging, X-ray imaging, tomosynthesis imaging, or X-ray diffraction imaging. In certain embodiments, all or a portion of the X rays from the source spot are physically shaped into a single, collimated, fan beam while intentionally altering the spectral distribution. For example, the spectrum may be altered for very low (<60 KeV) and/or very high (>200 KeV) energy ends of the source spectrum.

In the method and device disclosed herein, a minimum of three different materials are used in a graded multilayer stack to obtain increased total internal reflection over current practice by maximizing the difference in real refractive indices between successive layers, with the real refractive index decreasing in successive layers. In an embodiment that provides even greater total internal reflection, the ratio of the change in imaginary parts to the change in real refractive index between successive layers is minimized by simultaneously minimizing the change in the imaginary part and maximizing the real refractive index changes between successive layers. The imaginary part of the refractive index is related to the mass-energy absorption coefficient of the material in which the X ray is traveling. Additionally, each successive layer has higher X-ray mass-energy absorption properties, while the real refractive index decreases monotonically from layer to layer. These criteria provide for optimal changes in real refractive index and X-ray absorption properties than in current reflective X-ray optics materials.

Generally, the complex refractive index 'n' of a material at X-ray energies can be expressed as $n=1-\delta+i\beta$, where the term $(1-\delta)$ is the real part of the complex refractive index of the material and the parameter $\beta$ is the imaginary part of the complex refractive index and is related to the mass-energy absorption coefficient in the material. At X-ray energies, the real part of the refractive index is very close to unity and is therefore usually expressed in terms of its decrement $\delta$ from unity, with $\delta$ typically on the order of $10^{-6}$ or smaller.

For improved reflectivity, in one embodiment, the ratio of the change in $\beta$ to the change in $\delta$ between adjacent multilayer materials is generally minimized. For the purpose of this disclosure, a first layer is considered adjacent to a second layer when there are no other materials interposed between the first and second layers that have a real refractive index or a coefficient of absorption that are different from the respective real refractive indices or coefficients of absorption of the first and second layers. The graded multilayer optic may be adapted for use in redirecting an incident X-ray beam through total internal reflection as a reflected X-ray beam. The reflected X-ray beam may form a fan-shaped beam. The graded multilayer stack may comprise a plurality of multilayer zones. The graded multilayer optic device may be made by employing the techniques disclosed in the commonly assigned application titled "OPTIMIZING TOTAL INTERNAL REFLECTION MULTILAYER OPTICS THROUGH MATERIAL SELECTION" having application Ser. No. 12/469,121, which is incorporated by reference herein.

The graded multilayer optic sections stacked upon each other may have an exterior surface sloping between an input and an output face. In certain embodiments, each layer at the optic input (side closest to the source) may be curved at the same or different radius of curvature enabling the combined layers in the optic device to capture a large source solid angle and to redirect those source X rays into a highly collimated fan-shaped beam. As the higher refractive index layers curve towards the optic output, the X rays may be channeled down the layers of the graded multilayer optics. In one embodiment, a collection angle of the graded multilayer optic device is up to about 90 degrees. The collection angle of an optic device is defined as the maximum angle of emitted X-ray photons relative to the optic's major symmetry axis. In this example, a collection angle of 1 degree indicates that photons emitted by an X-ray source in a range from about 0 degrees to about 1 degree with respect to the optic's major symmetry axis are collected by the optic device. Likewise, a collection angle of 90 degrees indicates that source photons emitted in a range from about 0 degrees to about 90 degrees with respect to the optic device's major symmetry axis are collected by the optic device. In another embodiment, the layers of the graded multilayer optic device at the input face of the optic may be tapered to capture and redirect source X-rays into parallel beams in the direction perpendicular to the layers. In this embodiment, the fan shape may be in a direction parallel to the plane of layers of the graded multilayer optic devices. An array of such graded multilayer optic devices may be stacked to collect a majority (e.g., about 60 percent to about 90 percent) of the X rays from the source, and to produce a set of parallel fan beams in a direction perpendicular to the plane of the fan. Alternatively, the graded multilayer optic devices may include pairs of stacked graded multilayer optic devices. In one example, one half of a pair may be positioned to be a mirror image of the other pair half.

It should be understood that the number of multilayer zones comprising the multilayer material stack are not limited in any way but is rather a function of the particular application for which the multilayer material stack is configured. For example, in the case of high-resolution industrial CT where the resolution is on the order of micrometers, the number of multilayers in the stack maybe less than ten layers. In other types of CT, where large optic collection angles are desired, the number of layers may be in the thousands. The multilayer material stack may comprise tens or thousands of multilayer sections. In addition to a high-index layer, a low-index layer, and a grading zone with one or more grading layers disposed between the high-index layer and the low-index layer, the multilayer optic device may also comprise an X-ray opaque cladding layer at the outermost surface of the optic device to prevent the emission of X-ray radiation from the interior of the optic device through the edges of the non-emitting face of the device. The X-ray opaque cladding layer may be disposed on the optic device such that X-rays enter the optic device through the input face and exit the optic device substantially through the optic output face.

Typically, high refractive index materials transmit X rays with minimal losses, whereas, low refractive index materials substantially block X-ray transmission. When X rays encounter the interface between a high and low refractive index material, the X rays are reflected back into the high refractive index material with high efficiency if the X rays are traveling from the high to low refractive index material, the difference in X-ray absorption between the materials is minimal, and if the X ray angle of incidence at the interface is less than the critical angle for total internal reflection. The value of the critical angle depends on the materials and the incident X-ray energy. The use of the graded multilayer optic device enables X rays of desired energies to be reflected via total internal reflection with high efficiency. Shaping the layers with the appropriate curvature and fabricating them with the appropriate thicknesses may produce a fan-shaped output beam that is highly collimated.

The width of the incident X-ray beam may be smaller or greater than a thickness of one multilayer section. When the width of the incident X-ray beam is greater than the thickness of one multilayer optic device, different parts of the incident X-ray beam may pass through and be totally internally reflected by some or all of the multilayer sections within the optic device, and emerge from the multilayer sections as corresponding parts of the reflected photon beam. Alternatively, when the width of the incident photon beam is smaller than the thickness of one optic device, the device may produce smaller flux gains but can provide useful redirection capabilities.

The graded multilayer optic devices may be utilized in applications that operate at energy levels above 60 keV, such as, for example, computed tomography (CT) imaging, radiographic imaging, tomosynthesis imaging, and high-energy X-ray diffraction imaging. Some of these applications may operate at energy levels as high as megavolt photon energies. In certain embodiments, silicon may be used as the high refractive index material for higher energy (on the order of megavolts) applications. Whereas, one or more of boron, beryllium, and lithium hydride may be used for the high refractive index material for relatively lower energy X rays. For example, one or more of boron, berellium, lithium hydride may be used for X-ray energies between 60 KeV and 100 KeV. For medical applications, the energy may be less than 140 KeV. Low refractive index materials for X-ray energies of 140 KeV or less may be selected from tungsten, irradium, platinum, or osmium. Depending on the materials used to fabricate the graded multilayer optic device, X-ray energies up to 10 MeV may be transmitted.

In certain embodiments, the X-ray beam is spectrally shaped using the graded multilayer optic device. In case of a Bremsstrahlung spectrum incident on the optic device, since the refractive indices of the alternating layers determine the energy cutoff above which reflection is prohibited, the highest energies in the Bremsstrahlung are cutoff, resulting in a narrower emitted energy spectrum than that of a normal Bremsstrahlung spectrum. Also, depending on the shape of the input and output faces of the optic device, the very low energy part of the emitted spectrum may be substantially reduced or eliminated.

In certain embodiments, the reflected X-ray beam from the multilayer optics may form a substantially collimated, fan-shaped beam having a desired spectral shape from a substantially divergent, collimated, or convergent input X-ray beam. In one example, the fan-shaped beam may include a continuous fan-shaped beam, or a discrete stack of parallel fan-shaped beams. In one example, a continuous fan-shaped beam may include overlapping outputs of two or more graded multilayer optic devices, and discrete fan-shaped beams may include non-overlapping outputs of the two or more graded multilayer optic devices. In one embodiment, the multilayer optics may produce a quasi-parallel monochromatic fan-shaped beam. Such a monochromatic fan-shaped beam with sufficient intensity may be employed in medical imaging and interventional treatments. Such monochromatic imaging may help reduce a patient's dose of X rays, while increasing the resolution and reducing artifacts, such as beam hardening, which result from the use of polychromatic X-ray spectra for imaging. The quasi-parallel nature of the fan-shaped beam produced by the optic devices may reduce the reconstruction artifacts that result from the divergent nature of the fan-shaped beams currently used in CT. The multilayer optics provide for the collection and redirection of an X-ray source's radiation over a larger source solid angle than otherwise possible. When applied to medical imaging systems, this may allow for decreased imaging exposure time and patient dose, simplify image analysis, and potentially improve diagnostic accuracy for imaging modalities such as computed tomography (CT). Moreover, for X-ray applications, the X-ray source may be operated at, for example, two to ten times less power, extending the life of the X-ray source.

The graded multilayer optic device provides an advantage in terms of spatial scale and flexibility. Due to the nature of the micro-fabricated, layered structure, the optic devices can be very small. In one example, a cross sectional size of the devices may be as small as tens of micrometers. The small scale means that an array, or a composite, of the graded multilayer optic devices with the same spectral emission characteristics and geometry may be assembled within an area about the beam spot size used in most medical and industrial X-ray imaging (0.5-1.0 mm) to produce a large continuous or discrete beam of collimated fan beams.

In certain embodiments, the graded multilayer optic devices of the invention are employed in an X-ray imaging system, such as a CT system, an X-ray radiographic system, a tomosynthesis system, or an X-ray diffraction system. The imaging system includes a target that has at least one target focal spot. The imaging system includes one or more graded multilayer optic devices in communication with the target to transmit at least a portion of the X rays through total internal reflection to produce one or more fan-shaped beams. The graded multilayer optic devices include a first graded multilayer section for redirecting and transmitting X rays through total internal reflection. The first graded multilayer section includes a high-index layer of material having a first complex refractive index $n_1$. The first complex refractive index $n_1$ includes a real part $Re(n_1)$ of the first complex refractive index and an imaginary part $\beta_1$ of the first complex refractive index. The real part $Re(n_1)$ of the first complex refractive index may also be represented as $(1-\delta_1)$. The first graded multilayer section further includes a low-index layer of material having a second complex refractive index $n_2$. The second complex refractive index includes a real part $Re(n_2)$ of the second complex refractive index and an imaginary part $\beta_2$ of the second complex refractive index. The real part $Re(n_2)$ of the second complex refractive index may also be represented as $(1-\delta_2)$. The first graded multilayer section also includes a grading zone disposed between the high-index layer of material and the low-index layer of material. The grading zone includes a grading layer having a third complex refractive index $n_3$. The third complex refractive index $n_3$ includes a real part $Re(n_3)$ of the third complex refractive index and an imaginary part $\beta_3$ of the third complex refractive index. The real part $Re(n_3)$ of the third complex refractive index may also be represented as $(1-\delta_3)$ such that $Re(n_1)>Re(n_3)>Re(n_2)$. As used herein, the term "imaginary part of the complex refractive index" corresponds to the mass-energy absorption coefficient.

The target may be enclosed within a housing having an X-ray transparent window. The graded multilayer optic device may be mounted within or exterior to the housing device. In one embodiment, a graded multilayer optic device may be optically coupled to the window, either interior or exterior to the housing. In one example, the window may be integrated with the graded multilayer optic device. In other words, the graded multilayer optic device may be a part of the window. In the case of transmission targets, the graded multilayer optic device may be mounted on the target or integral to the target. Alternatively, in case of reflection targets the graded multilayer optic device may be disposed proximate to the target.

It is known that target focal spots are not completely static and can move dynamically, in some cases by tenths of a millimeter or more. An array of graded multilayer optic devices may be designed and positioned to compensate for movement of one or more focal spots. For example, the optic core, and the optic layers near the core may be designed to efficiently collect X rays from a focal spot that has moved less than or equal to 100 microns, which is a typical range of focal spot movements. Also the optic array can be made larger than the focal spot, so that when the focal spot moves the whole spot will still be covered with optics. It should be appreciated that the array may cover less than the entire target focal spot and still function efficiently. In one example, each of the graded multilayer optic devices is fabricated such that the width of the graded multilayer optic device is sufficient to optically cover the extent of the target spot with enough extra coverage to compensate for any likely movement of the target spot. Each of the graded multilayer optic devices can be fabricated to different widths and stacked, or they can all be fabricated to the same width and stacked.

FIG. 1A is a diagrammatical cross-sectional illustration of an exemplary embodiment of a single graded multilayer section 140 comprising a high-index layer 142, a low-index layer 144, and a grading zone 158 having a plurality of grading layers 152, 154, and 156 disposed between the high-index layer 142 and the low-index layer 144. As noted above, thicknesses of the material layers are exaggerated for clarity of illustration. A first reflecting interface 162 is formed between the high-index layer 142 and the first grading layer 152. Similarly, a second reflecting interface 164 is formed between the first grading layer 152 and the second grading layer 154; a third reflecting interface 166 is formed between the second grading layer 154 and the third grading layer 156; and a fourth reflecting interface 168 formed between the third grading layer 156 and the low-index layer 144.

A divergent X-ray radiation beam 172 may be provided by an X-ray radiation source 170 to irradiate an input face 146 of the graded multilayer zone 140. Although the X-ray beam 172 is shown in the illustration as five diverging X-ray beamlets 172-0 through 172-4, it should be understood that the X-ray beam 172 is physically a continuous beam distributed over a specified solid angle of emission, and that the representation of the X-ray beam 172 as discrete beamlets is made only to facilitate the presentation of the various exemplary embodiments herein. In an exemplary embodiment, the graded multilayer section 140 is configured to include a redirection section 174 and a collimation section 176, generally configured as shown. The redirection section 174 functions to substantially redirect and collimate the divergent X-ray beam 172 as a substantially collimated beam 178 to a desired region of space. The collimation section 176 provides further collimation of the beam exiting the redirection section 174.

The first reflecting interface 162 is represented as having a curved portion in redirection section 174 continuous with a substantially straight portion in collimation section 176 in the cross-sectional view of FIG. 1A. It should be understood that, physically, the first reflecting interface 162 forms a surface for reflection of the X-ray beamlet 172-1 and may comprise, for example, a planar, cylindrical, or conical surface, a combination of these surfaces, or a more complex curved surface. The cross sections of the reflecting interfaces 164, 166, and 168 are similarly shown as curved lines in the redirection section 174 and as straight lines in the collimation section 176. The curved-line portions of the reflecting interfaces 164, 166, and 168 represent physical surfaces of positive curvature such as, for example, cylindrical surfaces for redirection or collimation of the divergent X-ray beam 172. Similarly, straight-line portions of the reflecting interfaces 164, 166, and 168 represent physical planar or cylindrical surfaces, or combinations of planar and cylindrical surfaces.

Collimation of the X-ray beam 172 can best be understood by following the transmission paths of the X-ray beamlets 172-0 through 172-4. As shown, the center of the X-ray source 170 is generally coincident with an axis disposed through the middle of the high-index layer 142. A zeroth X-ray beamlet 172-0 may pass through the high-index layer 142 to emerge as a zeroth collimated photon beamlet 178-0 without reflection, as shown. In comparison, the first X-ray beamlet 172-1 may pass through the high-index layer 142 with one or more total internal reflections, as indicated by an initial reflection point 182a and a final reflection point 182b, and emerge as a first collimated X-ray beamlet 178-1. If the second X-ray beamlet 172-2 impinges on the initial reflection point 184a at less than the critical angle, with respect to the second reflecting interface 164, the second X-ray beamlet 172-2 may undergo multiple total internal reflections along the curved portion of the second reflecting interface 164, before passing out of the first layer 152 in the grading zone as a second collimated photon beamlet 178-2. These multiple total internal reflections are represented in the illustration by an initial reflection point 184a and a final reflection point 184b, where the intermediate multiple total internal reflections occurring between the initial reflection point 184a and the final reflection point 184b are not shown, for clarity of illustration.

In an exemplary embodiment, the curvature of the curved portion of the second reflecting interface 164 between the initial reflection point 184a and the final reflection point 184b is specified such that all subsequent reflections of the second X-ray beamlet 172-2 from the reflecting interface 164, between the initial reflection point 184a and the final reflection point 184b, occur at less than the critical angle and are thus total internal reflections.

Similarly, the third X-ray beamlet 172-3 may undergo multiple total internal reflections between an initial reflection point 186a and a final reflection point 186b, and the fourth X-ray beamlet 172-4 may undergo multiple total internal reflections between an initial reflection point 188a and a final reflection point 188b. The curvatures of the curved portions of the third and fourth reflecting interfaces 166 and 168 are specified such that multiple total internal reflections may occur along the portions of the reflecting interfaces 166 and 168 lying in the redirection section 174. In an exemplary embodiment, an X-ray beamlet may undergo hundreds or thousands of reflections along a corresponding curved surface in the redirection section 174 before passing out of the multilayer section 140. It can be appreciated by one skilled in the art that the desired trajectories of the collimated X-ray beamlets 178-1 through 178-4 are achieved when the reflected beamlets pass from the redirection section 174 into the collimation section 176, that is, when the tangent to the curved portion of a layer at the end of the redirection section 174 is substantially parallel to the continuing linear section 176. The physical length of the collimation section 176 determines the degree of collimation desired or it can be specified so as to provide a convenient physical size for handling of the overall optic device. The final reflection point may occur in either of the redirection section 174 or the collimation section 176.

Figure 1B:
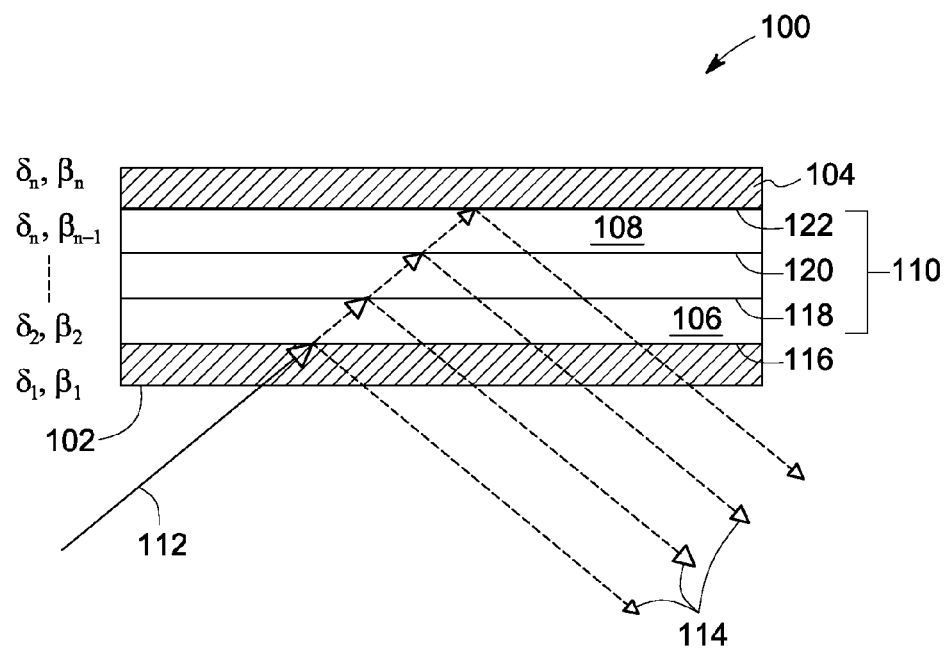
FIG. 1B is a diagrammatical view of a single grading section having n number of layers, with the first layer being the high-index material layer and the $N^{th}$ layer being the low-index material layer.

FIG. 1B illustrates an example of a single grading section 100 having N number of layers. In the illustrated embodiment, the first layer 102 is a high-index material layer, and the $N^{th}$ layer 104 is a low-index material layer. The layers between the first layer 102 and the $N^{th}$ layer 104 define a grading zone 110. As will be appreciated, while the simplistic model of total internal reflection suggests that all photons (represented by arrow 112) less than the critical angle are reflected (represented by arrow 114) with 100% efficiency, in reality a small percentage of X rays satisfying the total internal reflection condition may pass through the interface, such as interfaces 116, 118, 120 or 122, and may be transmitted into the underlying layer. The multiple layers in the intermediate grading zone 110 provide multiple opportunities for these transmitted X rays to undergo total internal reflection and be reflected out of the multilayer. In an optimal optic design, by the time the transmitted X rays reach the last layer, less than $10^{-4}$% of the photons incident on the interface between the first and second layers 102 and 106, respectively, may have reached the interface between the $(N-1)^{th}$ layer 108 and the $N^{th}$ layer 104. In an optimal graded multilayer design, 99.9999% or more of the incident photons in the first layer are reflected by the multiple layers in the graded multilayer section 100, producing a reflected beam of nearly the same intensity as the incident beam within the angular range from 0 degrees to the critical angle for total internal reflection.

The high-index layer 142 may be formed as a generally planar core or a substrate with a curved or cylindrical surface at one end, for producing the curved interfaces in the redirection section 174 of the graded multilayer zone 140. Other core configurations are also possible, such as a core layer having a first curved surface at one end of the core layer and a second curved surface at the other end.

Figure 2:
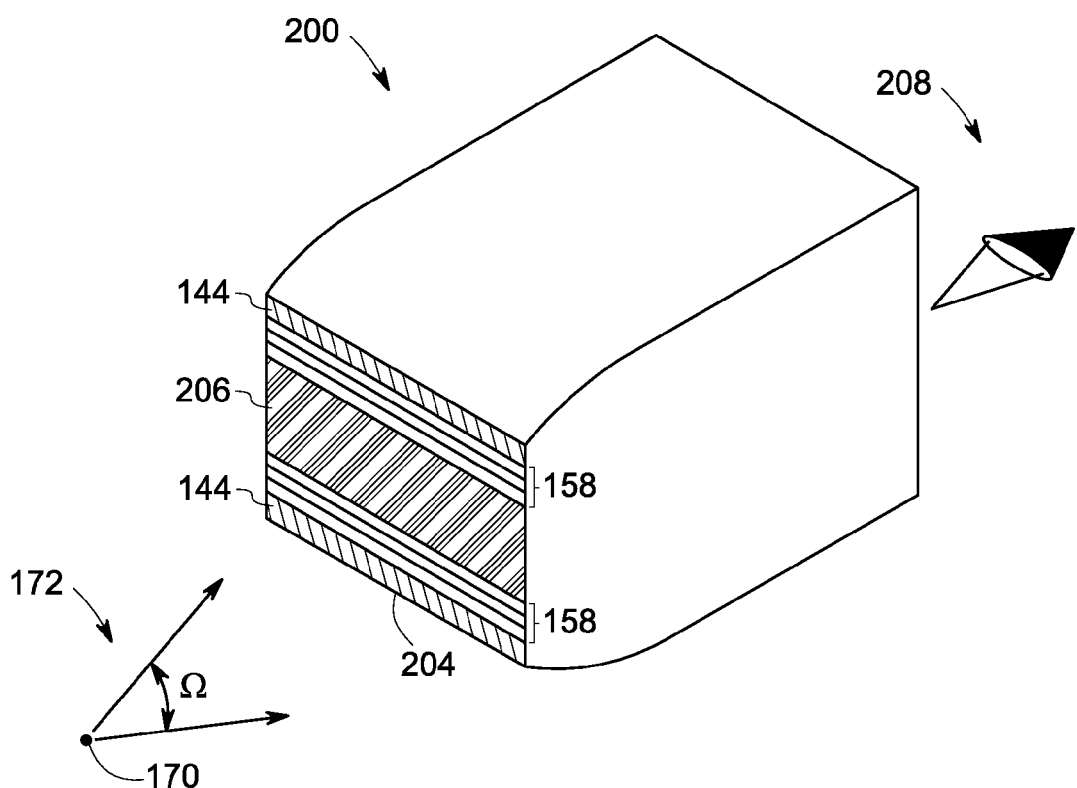
FIG. 2 is an isometric diagrammatical detail view of a multilayer optic device comprising graded multiple material layers used to form the output of a diverging X ray source into a collimated X-ray fan beam.

FIG. 2 is a simplified isometric diagrammatical representation of an optic device 200, here shown with the output of the divergent X-ray source 170 irradiating an input face 204. The optic device 200 may be used to form a fan-shaped collimated X-ray beam output 208, the collimated X-ray beam 208 substantially transmitted in a series of planes lying parallel to the longitudinal symmetry plane of the optic device 200. With reference to FIG. 1A, the optic device 200 of FIG. 2 may be fabricated by depositing grading zones 158 on both surfaces of a high-index layer 206, and then depositing low-index layers 144 on the grading zones 158. It can be appreciated that the optic device 200 is essentially a unitary combination of the multilayer section 140 (see FIG. 1A) with its mirror image.

Figure 3:
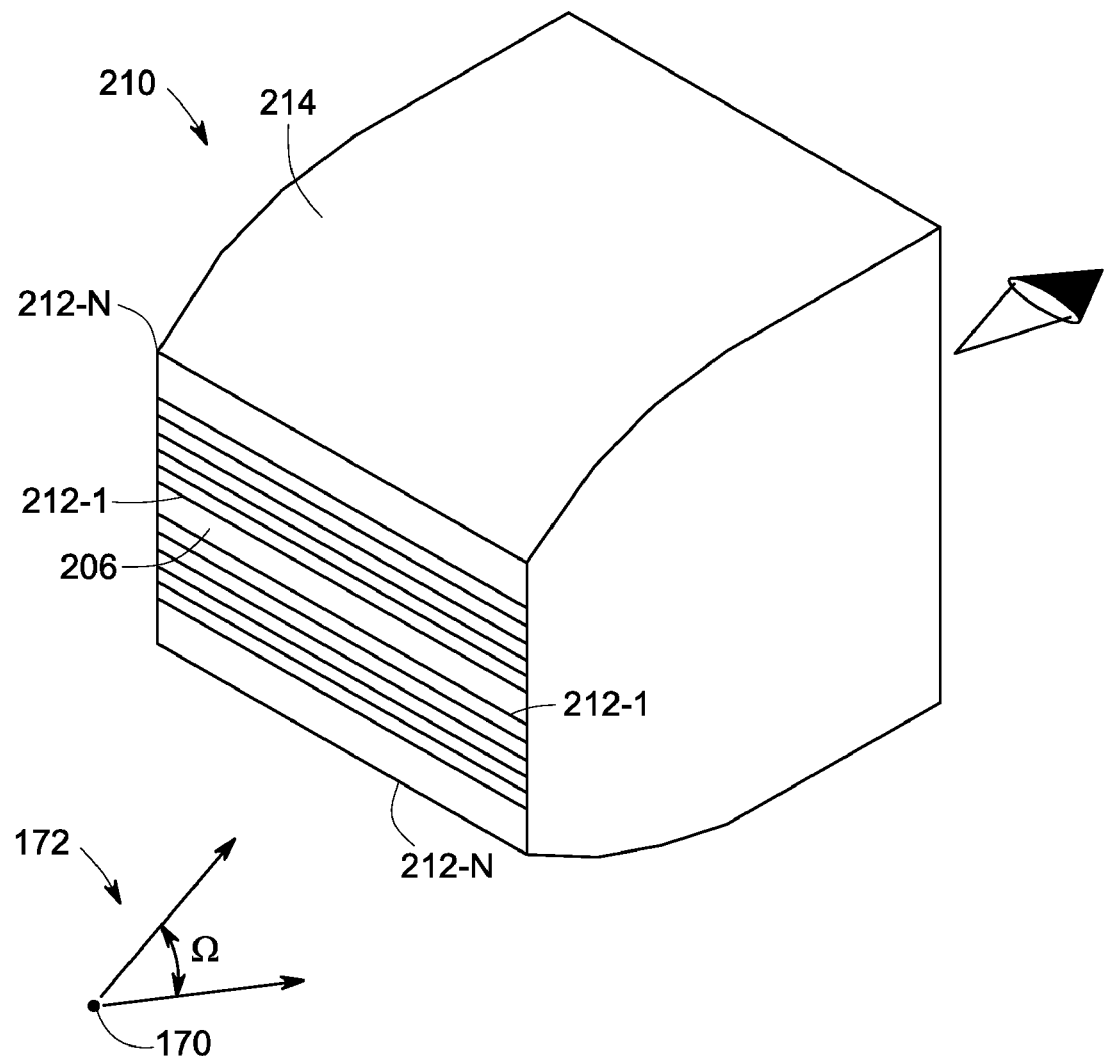
FIG. 3 is an isometric-diagrammatical detailed view of the optic device of FIG. 2 comprising additional graded multilayer sections.

By repeating the deposition of multilayers both above and below the high-index layer 206 of the optic device 200, a larger optic device 210 may be formed, as shown in FIG. 3. The optic device 210 thus includes the central high-index layer 206 over which a plurality of multilayer zones 212-1 through 212-N have been repeatedly deposited to yield a planar stack-up of tens, or hundreds, or thousands, or millions of multilayer zones, substantially as shown. Part of the multilayer zones 212-1 through 212-N comprise cylindrical surfaces to form a redirection section 214 that can function to redirect and collimate an incident divergent photon beam.

Figure 4:
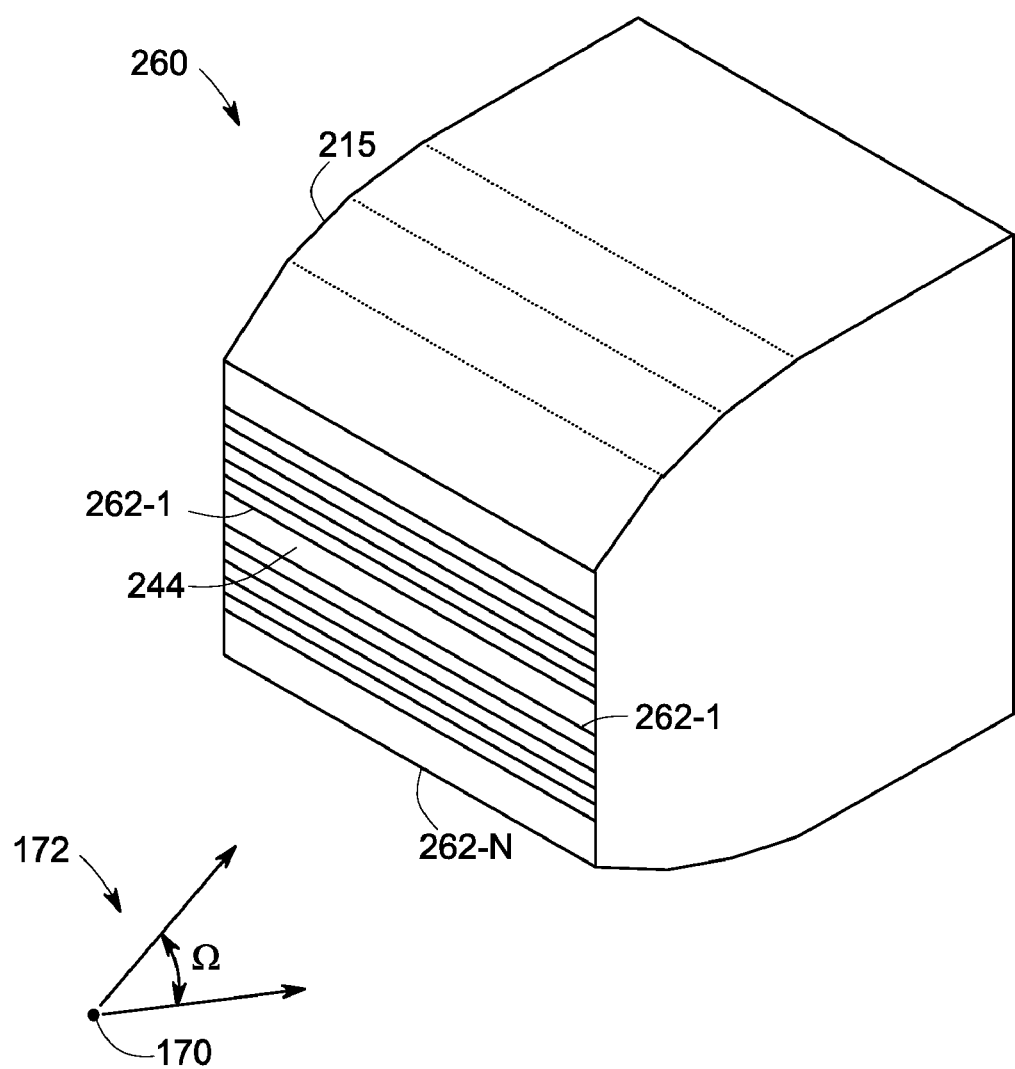
FIG. 4 is an isometric diagrammatical detailed view of an exemplary embodiment of a multilayer optic device comprising planar surfaces to approximate a curved surface.

There is shown in FIG. 4 an optic device 260 including the core layer 244. A plurality of planar multilayer zones 262-1 through 262-N have been serially deposited, both above and below the core layer 244, to yield a planar stack-up of tens, hundreds, thousands, or millions of multilayer zones, similar to the optic device 210 shown in FIG. 3. The re-direction section 215 may be a combination of two or more planar surfaces 248. The planar surfaces 248 may all have similar slopes and dimensions. Alternatively, the planar surfaces may vary in slopes and dimensions. For example, some of the planar surfaces 248 may be longer than others. Alternatively, some of the planar surfaces may make a steeper angle with respect to the core layer 244 than other planes. The planar surfaces 248 are arranged in a fashion such that the resultant surface 215 approximates a curved surface. Advantageously, the planar surfaces 248 are relatively simpler to fabricate as compared to their curved counter parts. Accordingly, forming a redirection section 215 as a combination of different planar surfaces simplifies fabrication.

Figure 5:
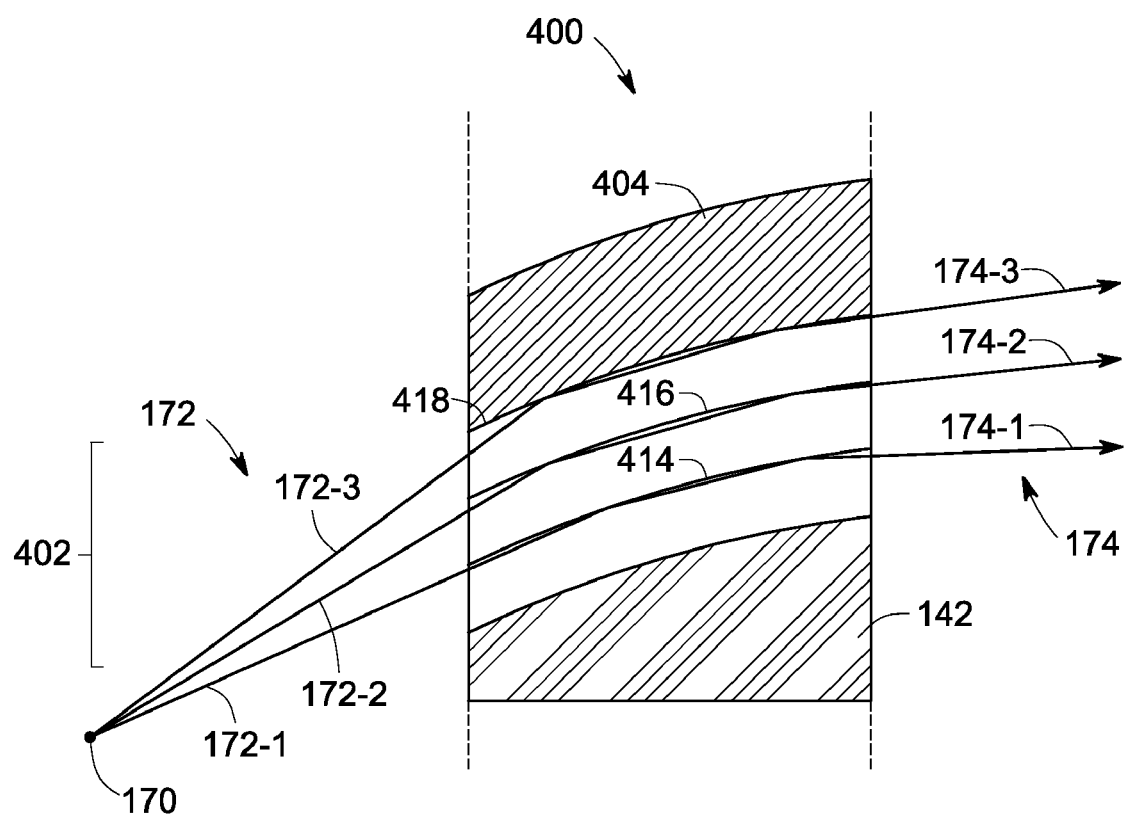
FIG. 5 is a detailed cross-sectional view of an exemplary embodiment of a single graded multilayer section configured to produce a substantially divergent X-ray beam output from a divergent X-ray beam input.

In an alternative aspect of the invention, shown in FIG. 5, an optic device 400 is configured to redirect the divergent input X-ray beam 172 emitted by the X-ray source 170 into a second divergent X-ray beam 174. The optic device 400 includes a graded multilayer section comprising a high-index layer, such as the high-index core 142, a grading zone comprising a plurality of grading layers 402 disposed on the high-index core 142, and a low-index layer 404 disposed on the grading zone 402. The optic device 400 comprises curved-line interfaces between the multiple layers. For a configuration in which the optic device 400 comprises a planar device, similar to the optic device 200 (see FIG. 2) or the optic device 210 (see FIG. 3), the low-index layer 404 forms a convex surface curved toward the longitudinal axis of the optic device 400.

It can be seen that for the curved reflection interfaces 414, 416, and 418, as shown in FIG. 5, tangents to the curved interfaces at the output face of the corresponding optic device will not be parallel to the optical axis of the optic device, unlike for the comparable curved portions of the reflection interfaces 164, 166, and 168 in the similarly-configured multilayer zone 140, shown in FIG. 1A. Accordingly, input X-ray beamlets 172-1, 172-2, and 172-3, in FIG. 5, are not sufficiently redirected inside the optic device 400 to form a collimated beam, and the output X-ray beam 174 in FIG. 5 remains divergent, although to a lesser degree than the input X-ray beam 172. In comparison, the divergent X-ray beam 172, in FIG. 1A, is substantially collimated by traveling through a redirection section 174 in which tangents to the curved reflection surfaces at the end of the redirection section 174 become parallel to an optic axis of the optic device and the straight line reflection surfaces in the collimation section 176.

Figure 6:
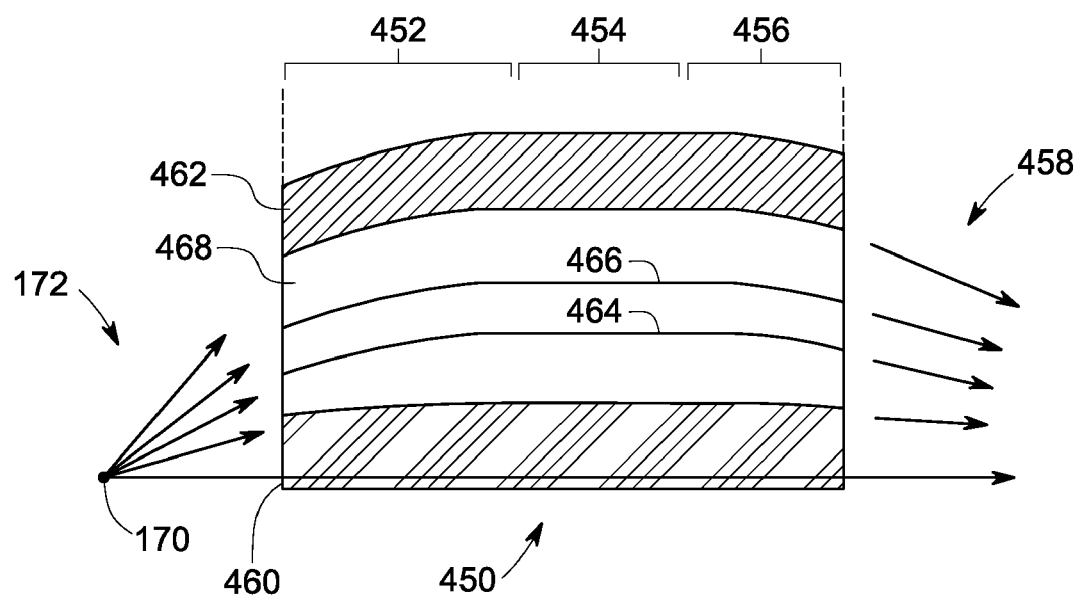
FIG. 6 is a detailed cross-sectional view of an exemplary embodiment of a single multilayer section configured to produce a substantially convergent X-ray beam output from a divergent X-ray beam input.

In another aspect of the invention, shown in FIG. 6, an optic device 450 is configured to redirect the divergent photon beam 172 into a substantially convergent output photon beam 458. The optic device 450 includes a first redirection section 452 and a second redirection section 456, and may or may not include an enclosed collimation section 454. A low-index layer 462 and a grading zone comprising layers 464, 466, and 468 in the redirection sections 452 and 456 have reflection surfaces curved toward a high-index layer 460 of the optic device 450.

Figure 7:
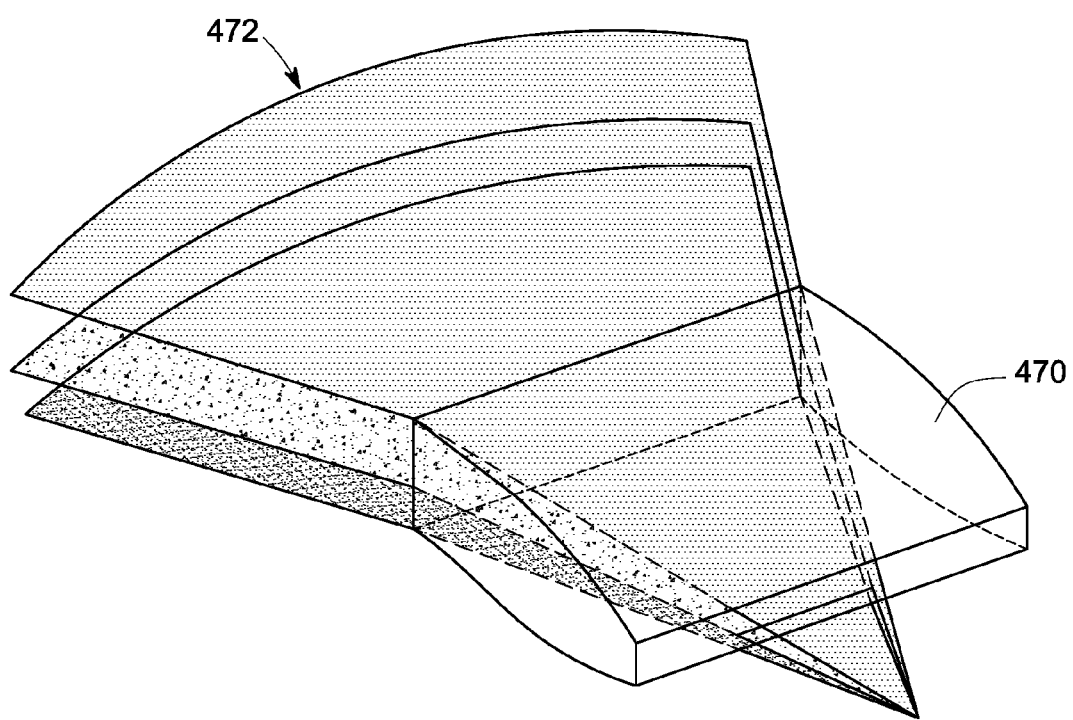
FIG. 7 is a schematic representation of a graded multilayer optic device having a rectangular cross section, wherein the optic device is used to produce a fan-shaped beam.
Figure 8:
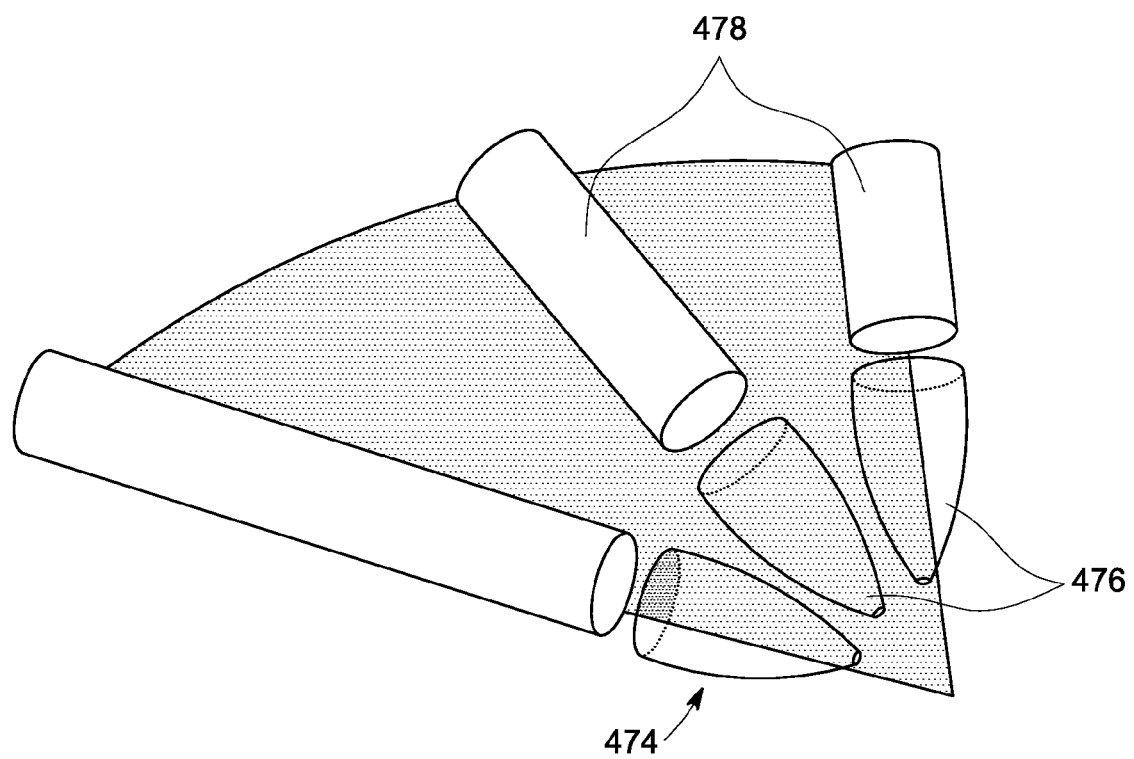
FIG. 8 is a schematic representation of one-dimensional array of graded multilayer optic devices each having a circular cross-section, wherein the optic devices are arranged to produce a fan-shaped beam.

In one embodiment, the graded multilayer optic devices are arranged in a two-dimensional array and configured to produce a fan-shaped beam profile. The various optic devices may be disposed at corresponding angles to form the two-dimensional array. A fan beam may be made of multiple circular cross-sectional beams that diverge from one another in the fan direction, as illustrated in FIG. 8. In another embodiment, each of the graded multilayer optic devices has a rectangular cross-sectional profile. As illustrated in FIG. 7, in this embodiment, the graded multilayer optic device 470 having a rectangular cross-section may produce a fan-shaped beam 472. FIG. 8 illustrates a one-dimensional array 474 of circular cross-section optics 476. The array 474 of circular cross-section optics 476 produces an approximate fan-shaped beam that consists of discrete cylindrical beams 478 arranged in a fan-shape.

Figure 9:
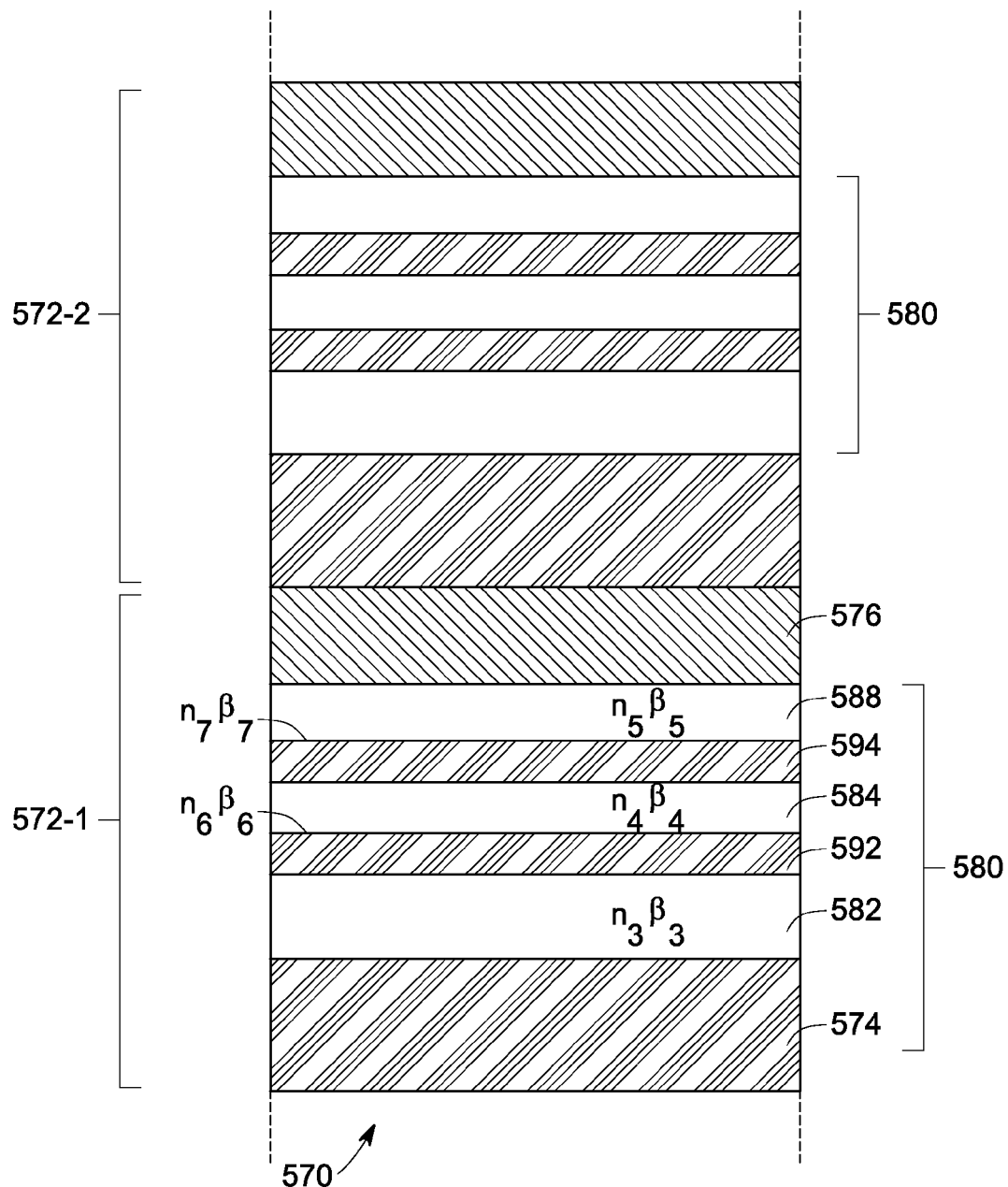
FIG. 9 is a detailed cross-sectional view of an exemplary embodiment of the graded multilayer material stack having multilayer sections with a high-index layer, a low-index layer, and a grading zone consisting of a plurality of grading layers with the same or different high-index layer interposed between pairs of grading layers.

Referring now to FIG. 9, an exemplary embodiment of yet another alternative graded multilayer material stack 570 is shown, comprising a plurality of graded multilayer sections, here represented by a graded multilayer section 572-1 and a graded multilayer section 572-2. One or more of the plurality of multilayer sections may include in each multilayer section a high-reflectivity grading zone 580 disposed between a high-index layer 574, fabricated from a material having a high real part of a complex refractive index $n_1$, and a low-index layer 576, fabricated from a material having a low real part of a complex refractive index $n_2$. The high-reflectivity grading zone 580 comprises a first grading layer 582 having a complex refractive index $n_3$ and an imaginary part of the complex refractive index $\beta_3$, a second grading layer 584 having a complex refractive index $n_4$, an imaginary part of the complex refractive index $\beta_4$, and a third grading layer 586 having a complex refractive index $n_5$ and an imaginary part of the complex refractive index $\beta_5$. In one embodiment, $\text{Re}(n_1) > \text{Re}(n_3) > \text{Re}(n_4) > \text{Re}(n_5) > \text{Re}(n_2)$ and $\beta_1 < \beta_3 < \beta_4 < \beta_5 < \beta_2$. The high-reflectivity grading zone 580 further comprises a first high-index grading layer 592 comprising material having high real part of a complex refractive index $n_6$ disposed between the first grading layer 582 and the second grading layer 584, and a second high-index grading layer 594 comprising material having high real part of a complex refractive index $n_7$ disposed between the second grading layer 584 and the third grading layer 586, where $\text{Re}(n_6) > \text{Re}(n_3)$ and $\text{Re}(n_7)$ >Re($n_4$). In one embodiment, to provide optimal total internal reflection, additionally $\beta_3 > \beta_6$ and $\beta_4 > \beta_7$.

It should be understood that the high-index material used to form the first high-index grading layer 592 and the second high-index grading layer 594 may comprise the same material used to form the high-index layer 574, or may comprise different high-index materials. The configuration of the graded multilayer material stack 570 provides for increased X-ray transmission because layers of high real refractive index materials (i.e., relatively low photon absorption regions) are disposed in the high-reflectivity grading zone 580. This configuration can be applied to embodiments having cross-sections shown in FIG. 1 and FIG. 5, for example, to increase the open area of the respective optic device by, effectively, making alternate grading layers into transmission layers.

Figure 10:
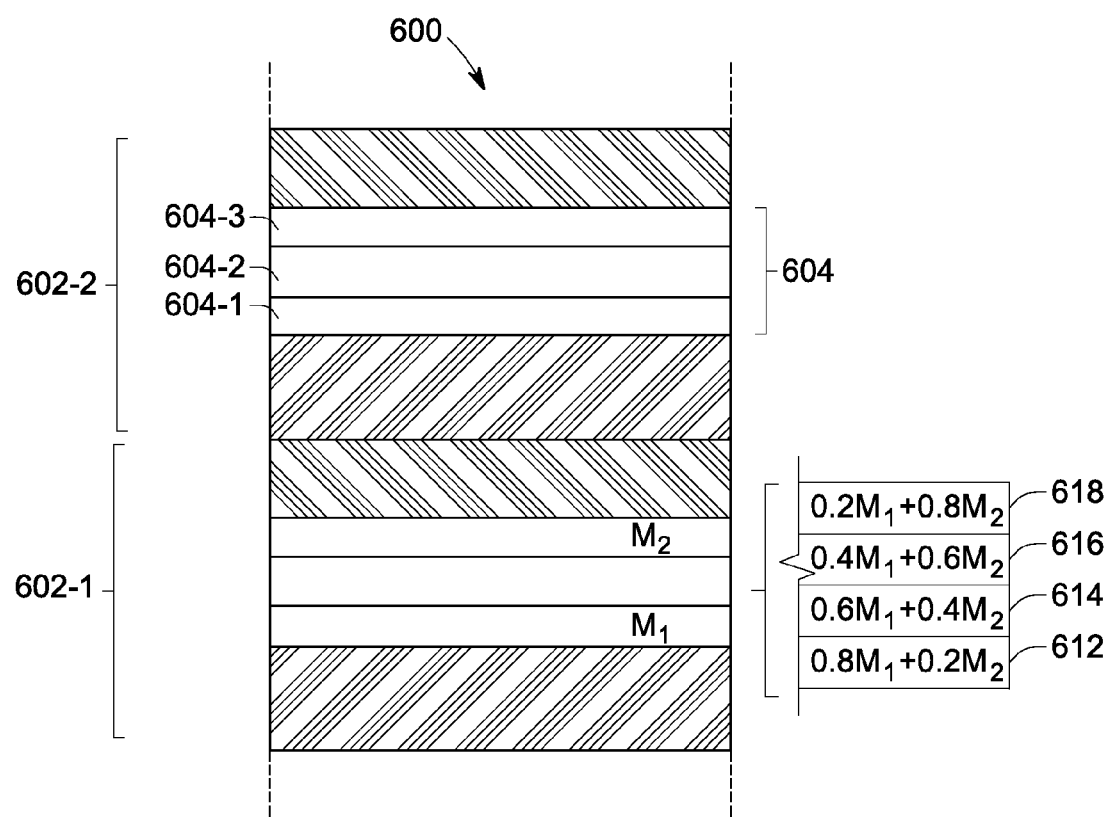
FIG. 10 is a detailed cross-sectional view of an exemplary embodiment of the graded multilayer material stack having one or more composite grading layers, wherein each composite grading layer comprises discrete grading sublayers, each grading sublayer including two component materials, each component material having a different real refractive index.

Referring now to FIG. 10, an exemplary embodiment of an alternative graded multilayer material stack 600 is shown, comprising a plurality of multilayer sections, exemplified by multilayer section 602-1 and multilayer section 602-2. One or more of the multilayer sections may include a grading zone 604 comprising grading layers 604-1 and 604-3, and a composite grading layer 604-2. The grading layer 604-1 comprises a first component material, denoted as $M_1$, having a unique complex refractive index $n_3$ and an imaginary part of the complex refractive index $\beta_3$, and the grading layer 604-3 comprises a second component material $M_2$ having a unique complex refractive index $n_5$ and an imaginary part of the complex refractive index $\beta_5$. In the exemplary embodiment shown, the composite grading layer 604-2 comprises four grading sublayers 612 to 618 as shown in the detail view on the right.

In the illustrated embodiment, each of the four grading sublayers 612 to 618 comprises a different composition of both first component material $M_1$ and second component material $M_2$ so as to provide a monotonic step-wise transition in optical characteristics between the grading layer 604-1 and the grading layer 604-3. The grading sublayer 612, for example, may comprise a mixture of about 0.8 by volume of first component material $M_1$ and about 0.2 by volume of second component material $M_2$, that is, the proportion of first component material $M_1$ to second component material $M_2$ in the grading sublayer 612 is about four to one by volume. Similarly, the grading sublayer 614 may comprise about 0.6 of first component material $M_1$ and about 0.4 of second component material $M_2$, the grading sublayer 616 may comprise about 0.4 of first component material $M_1$ and about 0.6 of second component material $M_2$, and the grading sublayer 618 may comprise about 0.2 of first component material $M_1$ and about 0.8 of second component material $M_2$.

It should be understood that a layer in the graded multilayer zone 604 may comprise more than one composite grading layer. Further, it should be understood that a composite grading layer may comprise two or more grading sublayers, and that the component material mixtures in the respective grading sublayers may contain proportions of the two grading layer component materials different from the examples provided above. Moreover, it should be understood that the compositional grading may also apply to the high-index layer and the low-index layer and need not be limited to only the grading zone. In general, given a layer 'A' having component material $M_A$ and a layer 'B' having component material $M_B$, a composite layer 'C' may be fabricated between the layer 'A' and the layer 'B' and may comprise a plurality of sublayers $C_1, C_2, \ldots C_N$. Preferably, the proportion of the layer component material $M_A$ in each of the sublayers $C_1, C_2, \ldots C_N$ decreases in successive sublayers between the layer A and the layer B, and the proportion of the layer component material $M_B$ increases in successive sublayers $C_1, C_2, \ldots C_N$ between the layer A and the layer B.

Figure 11:
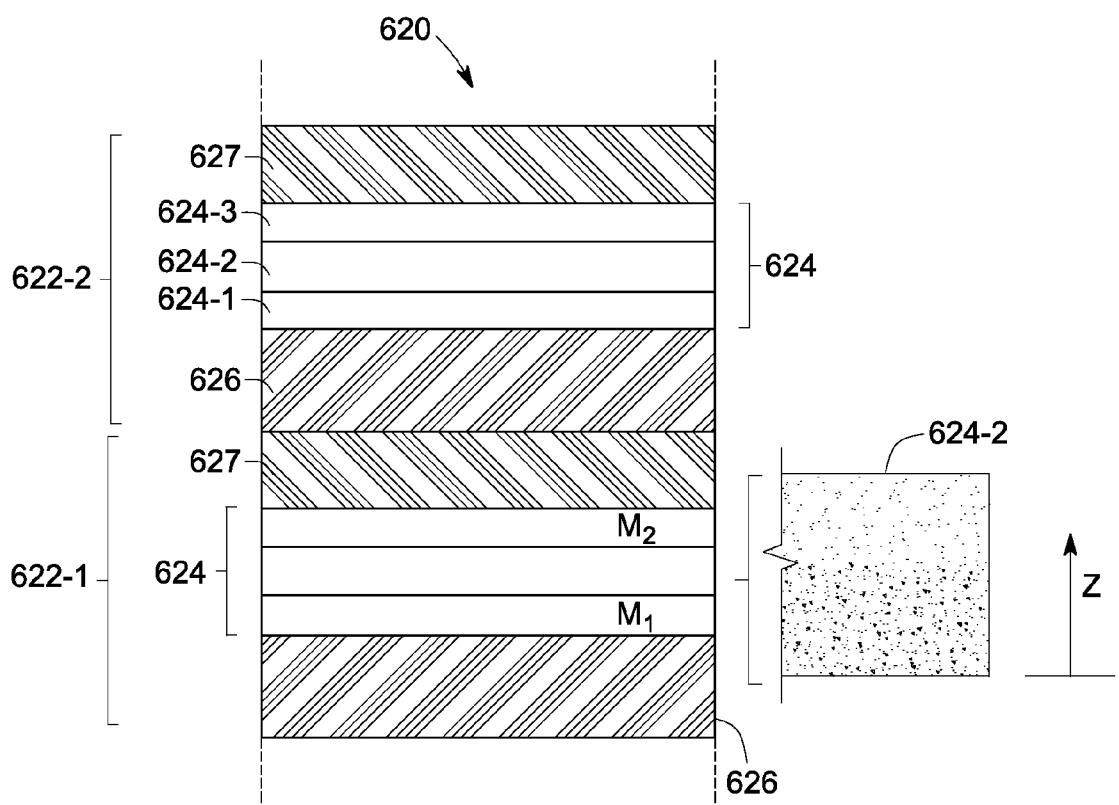
FIG. 11 is a detailed cross-sectional view of an alternative 10, showing a grading sublayer having a non-discrete distribution of the two component materials; exemplary embodiment of the graded multilayer material stack of FIG. 10.

There is shown in FIG. 11 a graded multilayer material stack 620, which is an alternative exemplary embodiment of the graded multilayer material stack 600 (see FIG. 10). The graded multilayer material stack 620 comprises a plurality of N graded multilayer sections, including a graded multilayer sections 622-1, and a graded multilayer sections 622-2 through an N-th multilayer sections (not shown). One or more of the graded multilayer sections may include a grading zone 624 with a composite grading layer 624-2. The composite grading layer 624-2 comprises a mixture of the first component material $M_1$ and the second component material $M_2$. The proportion of the first component material $M_1$ to the second component material $M_2$ deposited at different levels in the composite grading layer 624-2 may be specified as a function of the distance 'z' from a high-index layer 626 or from a low-index-layer 627. For example, the relative proportion of the component materials $M_1$ and $M_2$ at any point in the composite grading layer 624-2 may be expressed as a function of the parameter 'z' by:

$$\text{composite} = f(z)M_1 + [1-f(z)]M_2 \quad (13)$$

where f(z) may be, for example, a linear, polynomial, or logarithmic monotonic function, specifying fractional values for the component materials $M_1$ and $M_2$. The monotonic function thus produces a smooth compositional change of the relative proportion of the component materials $M_1$ and $M_2$ between the two adjacent grading layers 624-1 and 624-3.

Figure 12:
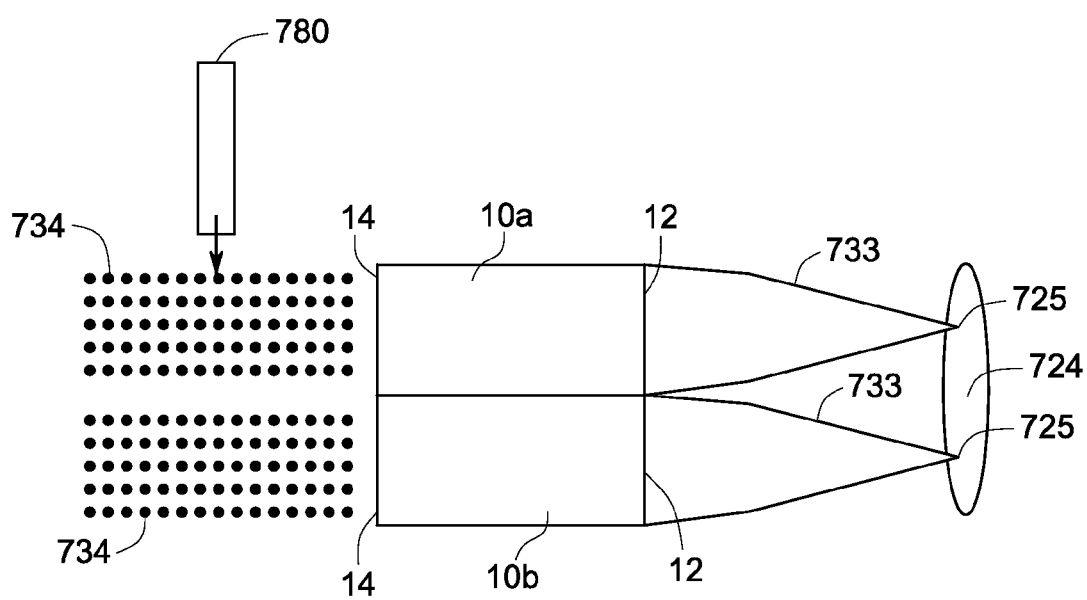
FIG. 12 is a schematic view of a pair of graded multilayer optic devices for use with a target in a dual energy scanning system in accordance with an embodiment of the invention.

Referring to FIG. 12, there is shown a pair of optic devices $10_a$ and $10_b$. Each of these optic devices $10_a$, $10_b$ is similar to the optic devices described with specific reference to FIGS. 1A-9. The pair of optic devices $10_a$, $10_b$ may be employed in a multi-energy X-ray imaging system. The system may include a first optic portion for redirecting first optic X rays through total internal reflection, and a second optic portion for redirecting second optic X rays, where the second optic X rays are at a different energy level than the first optic X rays. For example, the first optic portion is configured for producing a high-energy first optic energy spectrum, and the second optic portion is configured for producing a low-energy second optic energy spectrum. In this example, the mean energy of the first optic energy spectrum is greater than the mean energy in the second optic energy spectrum. The mean energy of the spectrum is the computed average energy of the spectrum, wherein each energy bin in the spectrum is first weighted by the fraction of total photons emitted at that energy before computing the average.

The difference between the optic devices $10_a$, $10_b$ is that one is formed to pass higher X-ray energies, while the other is formed to pass relatively lower X-ray energies. Shaping or filtering the source spectrum with the optic devices $10_a$, $10_b$ offers the promise of rapidly producing spectral shapes with sharp higher-energy cutoffs on a sub-view basis, which improves material separation sensitivity and can eliminate most registration issues. The capabilities for producing spectra with desired spectral shapes and for producing them on a fast time scale makes such optic devices particularly useful for multi-energy imaging.

The multi-energy imaging system may also include a filtering mechanism for filtering out certain energies from a beam transmitted by the optic device. The filtering mechanism may be external to the optic device, or integral to the optic device. In one embodiment, the filtering mechanism, such as but not limited to, K-edge filters that provide a sharp low-energy cut-off for each optic $10_a$, $10_b$. One embodiment includes vapor depositing the K-edge filter directly onto either end of the optic $10_a$, $10_b$. Alternatively, the K-edge filter may be formed as a separate foil aligned with the output or input of the optic $10_a$, $10_b$. Then each optic $10_a$, $10_b$ would have its own different K-edge filter either integral to the optic or separate from it.

The optic devices $10_a$, $10_b$, which may be in a stacked arrangement as illustrated, are in optical communication with the target 724 of the X-ray tube head. Specifically, X rays 733 formed by striking electron beams at focal spots 725 on the target 724 are propagated from the focal spots 725 toward the input faces 12 of the optic devices $10_a$, $10_b$. Alternatively, the focal spots 725 may each be within separate individual target spots as opposed to the single continuous target spot 724 or on separate non-contiguous targets. The X rays 733 are then focused by the optical devices $10_a$, $10_b$, as described above, and exit the output faces as redirected X rays 734. This geometry can be replicated to produce an array of pairs of such spots, where a distributed array of X-ray source spots is to be utilized.

To assist in separating high- and low-energy X-ray signals, a number of options are possible. One such arrangement uses an optic device with and without a separate K-edge filter to produce two signals whose energy distributions are different from each other. This is done by taking an image with one optic device and then retaking the image with both the optic device and a K-edge filter to eliminate low energy photons. Subtracting the two, appropriately normalized, signals results in a signal with predominantly low energies, while the signal produced by the combined optic device and K-edge filter produces a signal with predominantly relatively higher energy photons.

Alternatively, two optic devices could be used in conjunction with at least one K-edge filter. The two optic devices are made of materials that result in X-ray redirection and transmission of two different photon energy ranges that may or may not overlap. Taking an image with these two optic devices, repeating with the optic devices and a K-edge filter that blocks transmission of the lower energies from the optic device that transmits the lower energies, and subtracting the two, appropriately normalized, images will result in an image derived from only the low energies passed by the optic that transmitted the lower energies. The lower energy spectrum image could be obtained by subtracting this higher energy spectrum image, appropriately normalized, from the image formed with photons from the combined two optic devices and K-edge filter. To create a sharper low energy cut-off in the lower energy image, a second K-edge filter could be included that blocks the lowest energy photons from that optic.

Another option that can provide even greater energy separation between the signals is to couple the optic devices to separate targets at different accelerating potentials and taking sequential images with X rays emitted by each accelerating potential/optic combination. Advantageously, spectral shaping facilitates optimizing the effectiveness of a multitude of X-ray inspection and scanning procedures otherwise required in CT or X-ray diffraction applications. Although discussed in terms of considering differences of images at multiple energies, standard projection-based and image-based energy sensitive decomposition methods may be utilized to characterize the effective atomic number of the imaged objects.

Figure 13:
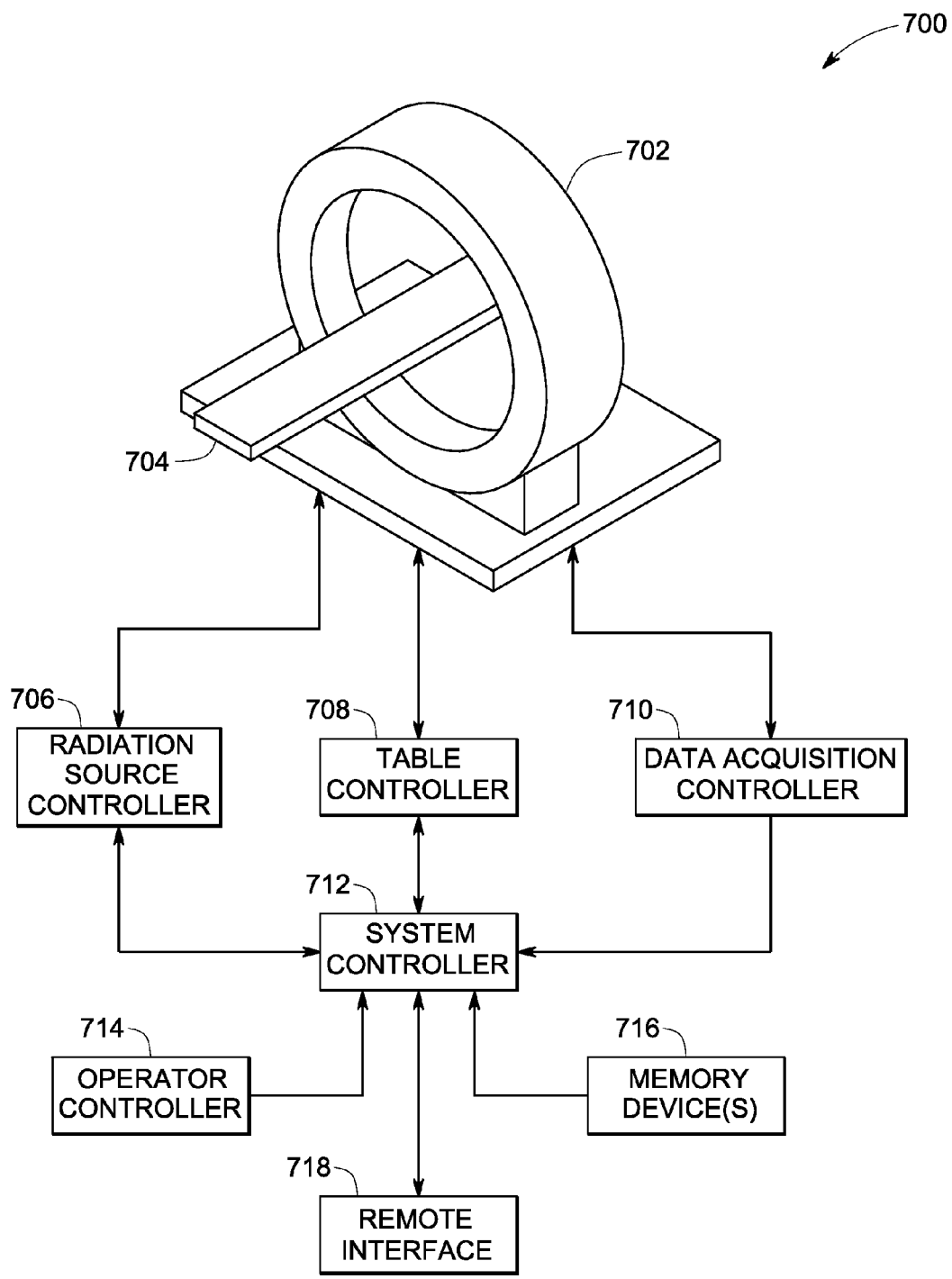
FIG. 13 is a diagrammatical representation of an example of a computed tomography imaging system employing the graded multilayer optic devices.

FIG. 13 illustrates a conventional acquisition system 700 for use in an object detection system, such as, for example, a computed tomography (CT) scanner. The acquisition system 700 comprises a scanner 702 formed of a support structure and internally containing one or more stationary or rotational distributed sources of X-ray radiation (not shown) and one or more stationary or rotational digital detectors (not shown), as described in greater detail below. The scanner 702 is configured to receive a table 704 or other support for an object to be scanned, such as, for example, patients, luggage, baggage or industrial parts baggage or luggage or patients. The table 704 can be moved through an aperture in the scanner to appropriately position the subject in an imaging volume or plane scanned during imaging sequences.

The system further includes a radiation source controller 706, a table/belt controller 708 and a data acquisition controller 710, which may all function under the direction of a system controller 712. The radiation source controller 706 regulates timing for discharges of X-ray radiation that are directed from points around the scanner 702 toward a detector element on an opposite side thereof, as discussed below. The radiation source controller 706 may trigger one or more emitters in a distributed X-ray source at each instant in time for creating multiple projections or frames of measured projection data. In certain arrangements, for example, the X-ray radiation source controller 706 may trigger emission of radiation in sequences to collect adjacent or non-adjacent frames of measured data around the scanner. Many such frames may be collected in an examination sequence, and data acquisition controller 710, coupled to detector elements as described below receives, signals from the detector elements and processes the signals for storage and later image reconstruction. In configurations described below in which one or more sources are rotational, the radiation source controller 706 may also direct rotation of a gantry on which the distributed source or sources are mounted. Table/belt controller 708, then, serves to appropriately position the table and subject in a plane in which the radiation is emitted, or, in the present context generally within a volume to be imaged. The table may be displaced between imaging sequences or during certain imaging sequences, depending upon the imaging protocol employed. Moreover, in configurations described below in which one or more detectors or detector segments are rotational, data acquisition controller 710 may also direct rotation of a gantry on which the detector or detectors are mounted.

System controller 712 generally regulates the operation of the radiation source controller 706, the table controller 708 and the data acquisition controller 710. The system controller 712 may thus cause radiation source controller 706 to trigger emission of X-ray radiation, as well as to coordinate such emissions during imaging sequences defined by the system controller. The system controller may also regulate movement of the table/belt in coordination with such emission to collect measurement data corresponding to volumes of particular interest, or in various modes of imaging, such as helical modes. Moreover, system controller 712 coordinates rotation of a gantry on which the source(s), detector(s), or both are mounted. The system controller 712 also receives data acquired by data acquisition controller 710 and coordinates storage and processing of the data.

It should be borne in mind that the controllers, and indeed various circuitry described herein, may be defined by hardware circuitry, firmware or software. The particular protocols for imaging sequences, for example, will generally be defined by code executed by the system controllers. Moreover, initial processing, conditioning, filtering, and other operations required on the measurement data acquired by the scanner may be performed in one or more of the components depicted in FIG. 13. For example, as described below, detector elements will produce analog signals representative of depletion of a charge in photodiodes positioned at locations corresponding to pixels of the data acquisition detector. Such analog signals are converted to digital signals by electronics within the scanner, and are transmitted to the data acquisition controller 710. Partial processing may occur at this point, and the signals are ultimately transmitted to the system controller for further filtering and processing. Additionally, the controllers may be implemented as separate entities, or they may be included as a single piece of hardware, firmware or software.

System controller 712 is also coupled to an operator interface 714 and to one or more memory devices 716. The operator interface may be integral with the system controller, and will generally include an operator workstation for initiating imaging sequences, controlling such sequences, and manipulating measurement data acquired during imaging sequences. The memory devices 716 may be local to the imaging system, or may be partially or completely remote from the system. Thus, imaging devices 716 may include local, magnetic or optical memory, or local or remote repositories for measured data for reconstruction. Moreover, the memory devices may be configured to receive raw, partially processed or fully processed measurement data for reconstruction.

System controller 712 or operator interface 714, or any remote systems and workstations, may include software for image processing and reconstruction. As will be appreciated by those skilled in the art, such processing of CT measurement data may be performed by a number of mathematical algorithms and techniques. For example, conventional filtered back-projection techniques may be used to process and reconstruct the data acquired by the imaging system. Other techniques, and techniques used in conjunction with filtered back-projection may also be employed. In one example, diffraction analysis is performed and at least one of the crystal structure, composition, and stress/strain of an object is identified.

A remote interface 718 may be included in the system for transmitting data from the imaging system to such remote processing stations, viewing stations, or memory devices.

In some embodiments, the target 724 (see FIG. 12), such as a rotatable or stationary target may be used in a computed tomography system. The target 724 includes a single target focal spot or a plurality of target focal spots 725. Further, the target 724 is enclosed within a vacuum housing (not shown) that includes at least one X-ray transmissive window. The target 724 can be rotated such that a target focal spot 725 is positioned in optical communication with one of the windows. The target focal spots 725 on the target 724 are generated from electrons that are accelerated toward the target; the electrons are emitted from one or more electron emitters.

It can be appreciated by one skilled in the art that any of the graded multilayer optical devices 172, 200, 210, 215, 400, 450, 570, 600 and 620 described above may comprise one or more of the graded multilayer section configurations described above, and further, wherein the central or core layer of a graded multilayer optic device may comprise either a high-index material or a low-index material, and an outer layer of the optic device may comprise a low-index material. Moreover, it should be understood that, although various core configurations and optic device embodiments disclosed herein comprise circular or planar cross sections, any core shape and optic device configuration may be used to produce the redirection of X-ray beams radiation without departing from the scope of the invention.

Advantageously, the graded multilayer optic device reduces or eliminates a tradeoff between X-ray flux utilization and reconstruction complexity that exists in any current CT imaging system. For example, the graded multilayer optic device mitigates the tradeoff between X-ray flux utilization and reconstruction complexity by providing a means to utilize a higher percentage of the available X-ray flux from the focal spot, while providing a topology that can employ 2D reconstruction principles. To accomplish this outcome, several graded multilayer optic devices are used to collect the available X rays and redirect them into a stack (discrete or continuous) of parallel fan beams. As a result, a high flux utilization may be achieved, while using simpler 2D reconstruction principles for suitable image quality. The graded multilayer optic devices significantly simplify the reconstruction strategies for high-resolution, high-throughput systems by eliminating the cone-beam reconstruction artifacts. These optics also would reduce detector costs by reducing the detector size required for a specified object coverage, as magnification issues in the longitudinal direction are eliminated. In addition to establishing planar sampling geometries, which enable the simpler, more accurate 2D reconstructions, an array of optics would also provide a uniform, consistent spectral shape, beamspot optical size, and beamspot location to all detector elements within a multislice array, reducing the variations of those parameters which are characteristic of the conventional single spot, wide-angle CT systems. As a result, next generation designs should feel the impact of these advantages. Better utilization of the available X-ray photons can also increase tube lifetime. Since more of the X-ray photons are available for imaging, the current in the electron beam striking the anode can be reduced. This effect reduces thermal cycling of the target, enables simpler cooling schemes, and provides longer tube lifetime.

Although discussed above in the context of CT imaging, benefits of multilayer X-ray optic devices such as better utilization of available X-ray photon and reduced thermal cycling of the target apply equally to X-ray imaging, tomosynthesis imaging and X-ray diffraction imaging.

This written description uses examples to disclose the invention and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An X-ray imaging system that produces one or more fan-shaped beams, comprising:
    a target for emitting X rays upon being struck by electrons from an electron source, said target comprising at least one target focal spot; and
    one or more graded multilayer optic devices in communication with said target to transmit at least a portion of said X rays through total internal reflection to produce said one or more fan-shaped beams, said graded multilayer optic devices, comprising:
        a first graded multilayer section for redirecting and transmitting X rays through total internal reflection including,
            a high-index layer of material comprising a first complex refractive index $n_1$ having a real part Re $(n_1)$ and an imaginary part $\beta_1$;
            a low-index layer of material comprising a second complex refractive index $n_2$ having a real part Re $(n_2)$ and an imaginary part $\beta_2$; and
            a grading zone disposed between said high-index layer of material and said low-index layer of material, said grading zone having a grading layer comprising a third complex real refractive index $n_3$ having a real part Re ($n_3$) and an imaginary part $\beta_3$ such that $Re(n_1)>Re(n_3)>Re(n_2)$.

2. The system of claim 1, wherein said target is enclosed within a housing having an X-ray transparent window, said one or more graded multilayer optic devices are mounted within the housing, mounted external to the housing, fabricated as the window, or integrated into the window.

3. The system of claim 1, wherein said one or more graded multilayer optic devices is mounted on said target for transmission targets or proximate to said target for reflection targets.

4. The system of claim 1, wherein said fan-shaped beam comprises a continuous fan-shaped beam or a discrete stack of parallel fan-shaped beams.

5. The system of claim 1, wherein said graded multilayer optic devices each have a collection angle of up to about 90 degrees.

6. The system of claim 1, wherein said one or more graded multilayer optic devices comprise a circular cross-sectional profile, and wherein the graded multilayer optic devices are arranged in one or two two-dimensional array to produce said one or more fan-shaped beams.

7. The system of claim 1, wherein each of the graded multilayer optic devices has a rectangular cross-sectional profile.

8. The system of claim 7, wherein said one or more graded multilayer optic devices comprises pairs of stacked graded multilayer optic devices, wherein one half of a pair is positioned to be a mirror image of the other half of the pair.

9. The system of claim 1, wherein said one or more graded multilayer optic devices are configured to compensate for movement of said at least one focal spot on said target.

10. The system of claim 1, wherein said X-ray imaging system is employed in one of a computed tomography (CT) system, an X-ray radiographic system, a tomosynthesis system, or an X-ray diffraction system.

11. The system of claim 1, wherein a ratio of a change in an imaginary part ($\beta$) of a complex refractive index to a change in a decrement ($\delta$) from unity of a real part ($1-\delta$) of a complex refractive index between adjacent multilayer materials is a minimum.

12. The system of claim 1, wherein the grading zone comprises a plurality of layers.

13. A multi-energy X-ray imaging system that produces one or more fan-shaped beams, comprising:
    an electron source;
    a target for forming X rays upon being struck by electrons from said electron source;
    a vacuum chamber housing the target;
    a window through which the X rays exit the vacuum chamber;
    at least one graded multilayer optic device configured to transmit a desired range of X-ray energies to produce the one or more fan-shaped beams, said at least one graded multilayer optic device comprises:
        a first optic portion for redirecting first optic X rays through total internal reflection; and
        a second optic portion for redirecting second optic X rays, said second optic X rays being at a different mean energy level than said first optic X rays.

14. The multi-energy X-ray imaging system of claim 13, wherein:
    said first optic portion is configured for producing a spectrum with a high mean energy; and
    said second optic portion is configured for a spectrum with a low mean energy, wherein the mean energy of said first optic energy spectrum is greater than or equal to the mean energy in the said second optic energy spectrum.

15. The multi-energy X-ray imaging system of claim 13, comprising a filtering mechanism for filtering out certain energies from a beam transmitted by said at least one optic device, wherein said filtering mechanism is at least one of a filtering mechanism external to said optic device and a filtering mechanism integral to said optic device.

16. A method for imaging an object, comprising:
    emitting electron beams from at least one electron beam emitter towards a target having at least one target focal spot;
    producing X rays from the target in response to being struck by the electron beams;
    forming the X rays into one or more fan-shaped beams, wherein the fan-shaped beams are produced via total internal reflection of the X rays through one or more graded multilayer optic devices positioned such that at least one of the one or more graded multilayer optic devices is in optical communication with the at least one target focal spot; and
    generating an image of the object by using the emitted X rays transmitted via the one or more graded multilayer optics.

17. The method of claim 16, further comprising filtering at least a portion of an energy spectrum.

18. The method of claim 16, further comprising two-dimensional (2D) reconstruction computations that are used to generate an image of the object.

19. The method of claim 16, further comprising performing computed tomography, tomosynthesis, X-ray diffraction or X-ray radiography of the object.

20. The method of claim 16, further comprising performing diffraction analysis and identifying at least one of the crystal structure, composition, and stress/strain of the object.

* * * * *